US008320999B2

(12) United States Patent
Ono

(10) Patent No.: US 8,320,999 B2
(45) Date of Patent: Nov. 27, 2012

(54) LEAK DETECTOR FOR DETECTING LEAK OF LIQUID INJECTED INTO BLOOD VESSEL USING PULSE SIGNAL

(75) Inventor: Seiichi Ono, Tokyo (JP)

(73) Assignee: Nemoto Kyorindo Co., Ltd., Tokyo (JP)

( * ) Notice: Subject to any disclaimer, the term of this patent is extended or adjusted under 35 U.S.C. 154(b) by 826 days.

(21) Appl. No.: 12/457,317

(22) Filed: Jun. 8, 2009

(65) Prior Publication Data

US 2010/0219959 A1  Sep. 2, 2010

Related U.S. Application Data

(62) Division of application No. 10/830,095, filed on Apr. 23, 2004, now Pat. No. 7,546,776.

(30) Foreign Application Priority Data

| Apr. 28, 2003 | (JP) | 2003-123460 |
| Nov. 7, 2003 | (JP) | 2003-378443 |
| Feb. 23, 2004 | (JP) | 2004-046555 |

(51) Int. Cl.
*A61B 6/00* (2006.01)
(52) U.S. Cl. ....................................... 600/475
(58) Field of Classification Search ................ 600/407, 600/473, 475, 476, 479; 73/597, 861.05, 73/861.27
See application file for complete search history.

(56) References Cited

U.S. PATENT DOCUMENTS

| 4,240,445 A | * | 12/1980 | Iskander et al. | 607/156 |
| 4,361,154 A | * | 11/1982 | Pratt, Jr. | 600/437 |
| 4,534,756 A | | 8/1985 | Nelson | |
| 4,541,281 A | * | 9/1985 | Chubachi et al. | 73/606 |
| 4,647,281 A | | 3/1987 | Carr | |
| 4,655,083 A | * | 4/1987 | Chubachi | 73/606 |
| 4,663,977 A | * | 5/1987 | Vander Heyden | 73/861.27 |
| 4,669,482 A | * | 6/1987 | Ophir | 600/449 |
| 4,710,163 A | | 12/1987 | Butterfield | |
| 4,773,267 A | * | 9/1988 | Abts | 73/597 |

(Continued)

FOREIGN PATENT DOCUMENTS

DE 37 32 399 10/1990

(Continued)

OTHER PUBLICATIONS

Polaschegg et al., "Hemodialysis machines and monitors," in Jacobs et al., *Replacement of Renal Function by Dialysis*, 1996, 10 pp.

*Primary Examiner* — John Fitzgerald
(74) *Attorney, Agent, or Firm* — Fitch, Even, Tabin & Flannery, LLP

(57) ABSTRACT

A leak detector sequentially emits pulse signals toward a human body at a position at which a needle is inserted, detects pulse signals reflected inside of the human body, and measures a time interval between the emission and the detection for each of the pulse signals. The leak detector then calculates the difference between the measured interval and a predetermined time interval, and generates a leak warning for notification when the difference exceeds an acceptable range. Since a swelling on the surface of the human body causes a path of the pulse signal to extend, the leak detector can detect, based on the extended signal path, that the needle has come off a blood vessel.

21 Claims, 16 Drawing Sheets

U.S. PATENT DOCUMENTS

| | | | |
|---|---|---|---|
| 4,877,034 A | 10/1989 | Atkins et al. | |
| 4,947,851 A * | 8/1990 | Sarvazyan et al. | 600/438 |
| 4,959,050 A * | 9/1990 | Bobo, Jr. | 604/505 |
| H924 H * | 6/1991 | Chimenti | 73/644 |
| 5,031,467 A * | 7/1991 | Rambow | 73/861.25 |
| 5,255,564 A * | 10/1993 | Glad et al. | 73/597 |
| 5,255,683 A * | 10/1993 | Monaghan | 600/458 |
| 5,313,947 A | 5/1994 | Micco | |
| 5,334,141 A | 8/1994 | Carr et al. | |
| 5,463,905 A * | 11/1995 | Baird | 73/861.25 |
| 5,741,980 A * | 4/1998 | Hill et al. | 73/861.04 |
| 5,767,409 A * | 6/1998 | Yamaguchi | 73/602 |
| 5,816,242 A * | 10/1998 | Cewers | 128/204.21 |
| 5,947,910 A | 9/1999 | Zimmet | |
| 5,954,668 A | 9/1999 | Uber, III et al. | |
| 5,964,703 A | 10/1999 | Goodman et al. | |
| 5,969,254 A * | 10/1999 | Yamaguchi | 73/602 |
| 6,009,380 A * | 12/1999 | Vecchio et al. | 702/142 |
| 6,012,324 A * | 1/2000 | Jakkula et al. | 73/19.03 |
| 6,062,091 A * | 5/2000 | Baumoel | 73/861.27 |
| 6,092,420 A * | 7/2000 | Kimura et al. | 73/620 |
| 6,295,873 B1 * | 10/2001 | Condreva | 73/597 |
| 6,360,611 B1 * | 3/2002 | Toda | 73/651 |
| 6,375,624 B1 | 4/2002 | Uber, III et al. | |
| 6,408,204 B1 | 6/2002 | Hirschman | |
| 6,487,428 B1 * | 11/2002 | Culver et al. | 600/310 |
| 6,644,119 B1 * | 11/2003 | Sinha | 73/579 |
| 7,047,058 B1 * | 5/2006 | Dvorsky et al. | 600/407 |
| 7,122,012 B2 * | 10/2006 | Bouton et al. | 600/587 |
| 2002/0004636 A1 | 1/2002 | Tsubata | |
| 2002/0172323 A1 | 11/2002 | Karellas et al. | |
| 2003/0036674 A1 * | 2/2003 | Bouton | 600/12 |
| 2003/0036713 A1 * | 2/2003 | Bouton et al. | 600/587 |
| 2006/0178616 A1 | 8/2006 | Hartman et al. | |

FOREIGN PATENT DOCUMENTS

| | | |
|---|---|---|
| DE | 40 13 402 | 11/1991 |
| DE | 92 11 933 | 1/1993 |
| DE | 196 09 698 | 9/1997 |
| DE | 197 34 002 | 9/1998 |
| DE | 197 46 377 | 7/1999 |
| DE | 198 09 945 | 9/1999 |
| DE | 100 51 943 | 5/2002 |
| EP | 0 330 761 | 12/1988 |
| EP | 0 332 330 | 9/1989 |
| WO | WO 97/10013 | 3/1997 |
| WO | WO99/15074 | 4/1999 |
| WO | WO99/26685 | 6/1999 |
| WO | WO 99/26686 | 6/1999 |

* cited by examiner

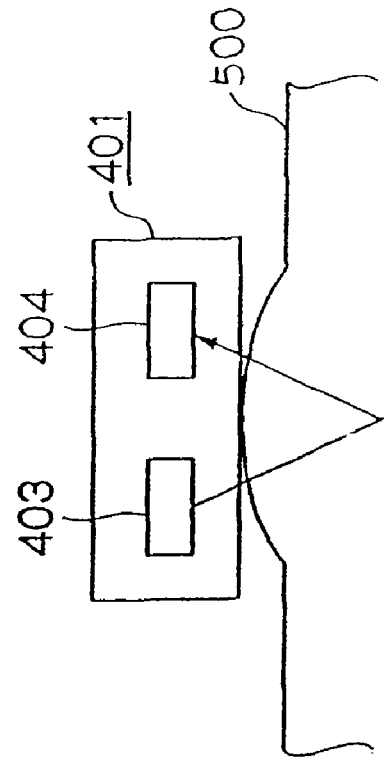
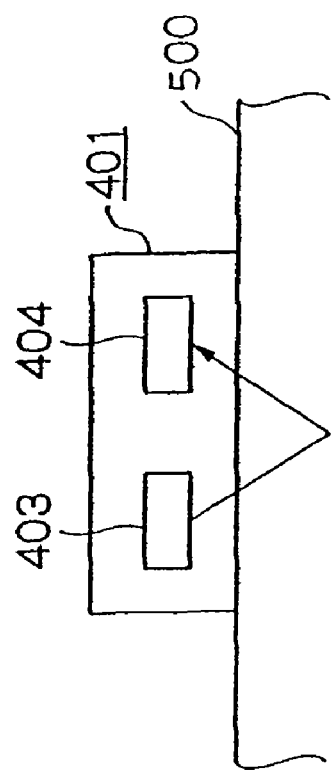

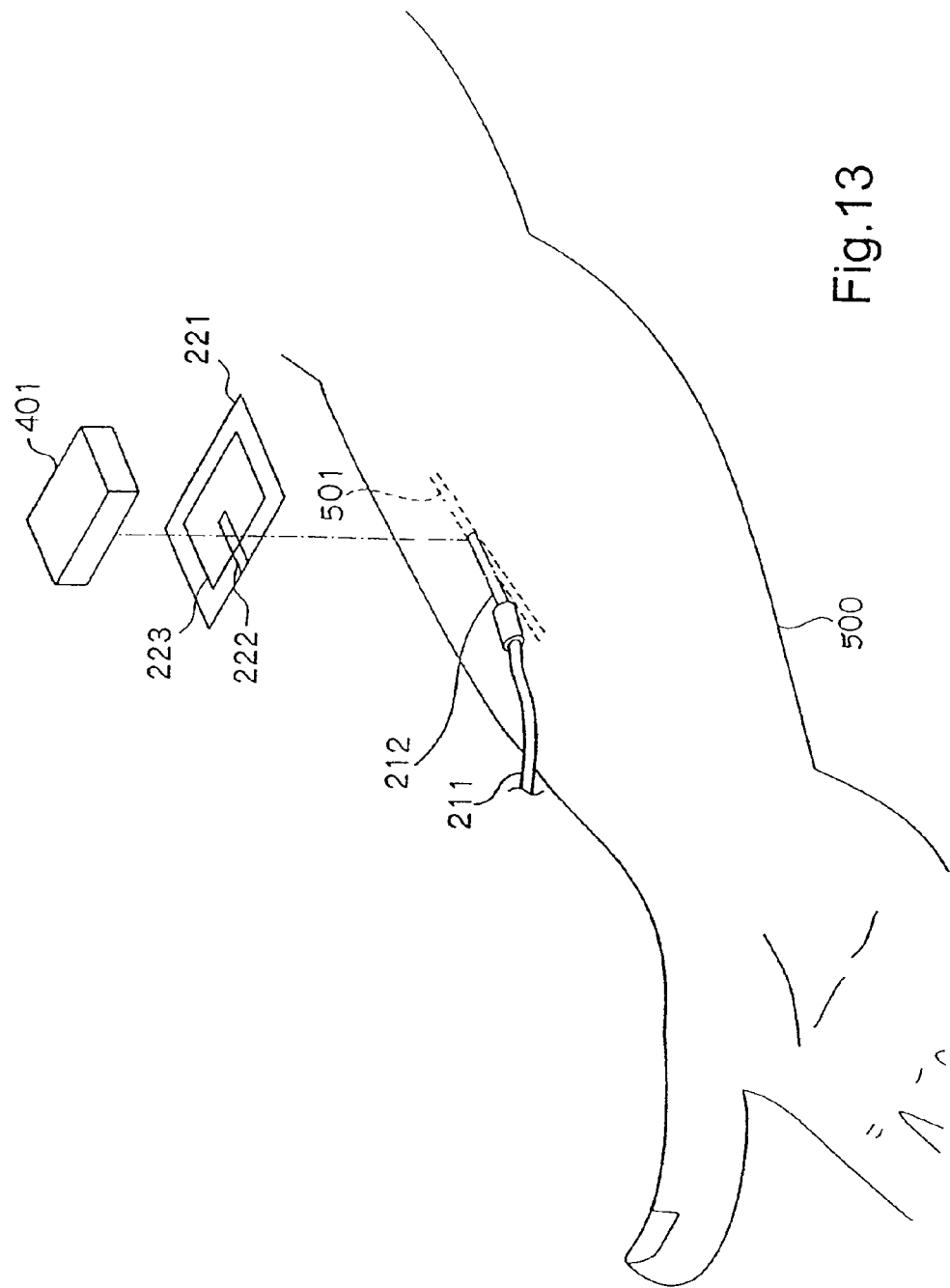

LEAK DETECTOR FOR DETECTING LEAK OF LIQUID INJECTED INTO BLOOD VESSEL USING PULSE SIGNAL

CROSS-REFERENCE TO RELATED APPLICATIONS

This is a divisional of U.S. application Ser. No. 10/830,095, filed Apr. 23, 2004, which issued as U.S. Pat. No. 7,546,776 on Jun. 16, 2009, and claims the benefit of foreign priority under 35 U.S.C. §119 based on Japanese Application Nos. 2003-123460, 2003-378443, and 2004-046555, filed respectively on Apr. 28, 2003; Nov. 7, 2003; and Feb. 23, 2004, the entire disclosures of which are hereby incorporated by reference.

BACKGROUND OF THE INVENTION

1. Field of the Invention

The present invention relates to a leak detector for detecting a leak or an extravasation of a liquid injected into a blood vessel near the surface of a human body by a syringe, and more particularly, to a leak detector for detecting a leak of a liquid injected by a liquid injector.

2. Description of the Related Art

Medical facilities currently used for imaging tomographic images of a patient include a CT (Computer Tomography) scanner, an MRI (Magnetic Resonance Imaging) apparatus, a PET (Positron Emission Tomography) apparatus, an ultrasonic diagnostic apparatus, and so on, and medical facilities currently used for imaging an angiogram of a patient include an angio apparatus, an MRA (MR Angio) apparatus, and so on. When a medical apparatus as listed above is used, a liquid such as a contrast medium, a balanced saline solution, and the like may be injected into a patient. A liquid injector has also been brought into practical use for automatically injecting a liquid. For example, the liquid injector employs a liquid syringe that is removably mounted, the liquid syringe comprises a cylinder member and a piston member slidably inserted in the cylinder member. The liquid injector has a syringe driving mechanism which presses the piston member into the cylinder member. The cylinder member, which is filled with a liquid, is coupled to a blood vessel near the surface of a human body through an extension tube and a needle, so that that the liquid in the liquid syringe is force-fed into the blood vessel of the human body by the liquid injector.

However, such a liquid injector automatically injects a liquid at a high pressure, so that even if the needle accidentally becomes detached from the blood vessel, for example, causing the liquid to leak under the skin, it is difficult for the operator to immediately recognize the leak.

To solve the problem as mentioned above, a variety of leak detectors have been proposed for detecting a leak or an extravasation of a liquid injected through a needle into a blood vessel of a human body, as described, for example, in U.S. Pat. Nos. 6,408,204, 5,964,703, 5,947,910, 6,375,624, 5,954,668, 5,334,141, 4,647,281, and 4,877,034. U.S. Pat. Nos. 6,408,204, 5,964,703, 5,947,910 disclose leak detectors for detecting a leaking liquid from a change in impedance on the surface of a human body; U.S. Pat. Nos. 6,375,624, 5,954,668, 5,334,141, 4,647,281 disclose leak detectors for detecting a leaking liquid from a change in temperature of a human organ; and U.S. Pat. No. 4,877,034 discloses a leak detector for detecting a leaking liquid from a change in optical characteristics of a blood.

However, all of these leak detectors have disadvantages of the need for a special sensor, a complicated structure, and a significant degradation in detection accuracy caused by disturbance.

SUMMARY OF THE INVENTION

The present invention has been made in view of the problem as mentioned above, and it is an object of the invention to provide a leak detector which is simple in structure and minimizes a degradation in detection accuracy due to disturbance.

A first leak detector according to the present invention is provided for detecting a leak of a liquid injected through a needle into a blood vessel near the surface of a human body, and includes pulse generating means, pulse detecting means, interval measuring means, difference calculating means, difference comparing means, and leak warning means. The pulse generating means sequentially emits pulse signals through wave propagation at a predetermined wavelength into the human body at a position at which the needle is inserted. The pulse detecting means detects pulse signals reflected inside of the human body. The interval measuring means measures a time interval between the emission and the detection for each of the pulses, and the difference calculating means calculates the difference between the measured time interval and a predetermined reference time interval. The difference comparing means compares the calculated difference with a predetermined acceptable range, and the leak warning means generates a leak warning for notification when the difference exceeds the acceptable range.

With the foregoing configuration in the first leak detector of the present invention, as the human body swells out on the surface due to a liquid leaking from a needle which has come off a blood vessel, the swelling causes a change in distance and time interval between the emission and the detection of the pulse signals reflected inside of the human body, so that the leak detector detects a leak of the liquid making use of the change in interval. With this approach, the accuracy of the detection is hardly degraded due to disturbance, and only a simple structure is required for the detection.

A second leak detector according to the present invention includes wavelength measuring means instead of the interval measuring means, wherein the wavelength measuring means measures the wavelength of a detected pulse signal, and the difference calculating means calculates the difference between the measured wavelength and a predetermined reference wavelength. Therefore, in the second leak detector of the present invention, as the human body swells out on the surface due to a liquid leaking from a needle which has come off a blood vessel, the swelling causes a change in wavelength of the wave propagation reflected inside the human body, so that the leak detector detects a leak of the liquid making use of the change in wavelength. With this approach, the accuracy of the detection is hardly degraded due to disturbance, and only a simple structure is required for the detection.

It should be noted that a variety of means referred to in the present invention are only required to be formed to implement functions associated therewith, and can be implemented, for example, by dedicated hardware for performing predetermined functions, a data processor provided with predetermined functions through a computer program, predetermined functions implemented by a data processor through a computer program, a combination of these, and the like.

Also, a variety of means referred to in the present invention need not be individually independent components, but may include a plurality of means formed into a single member, certain means included in another means as part thereof, part of certain means overlapping with part of another means, and the like.

BRIEF DESCRIPTION OF THE DRAWINGS

FIGS. 11a and 11b are schematic diagrams illustrating how an arm swells out with the leak detection unit mounted on the surface thereof;

FIG. 13 is a perspective view illustrating how the leak detection unit is mounted onto an arm using a modified adhesive pad;

DETAILED DESCRIPTION OF THE PREFERRED EMBODIMENTS

Configuration of Embodiment

One embodiment of the present invention will hereinafter be described with reference to the accompanying drawings. It should be first noted that in the following embodiment, front, rear, left, right, upward, and downward directions are defined as illustrated for description, but such definition of the directions is conveniently made for simplifying the description, and is not at all intended to limit the apparatus of the present invention to such directions during manufacturing, in use, and so forth.

Figure 3:
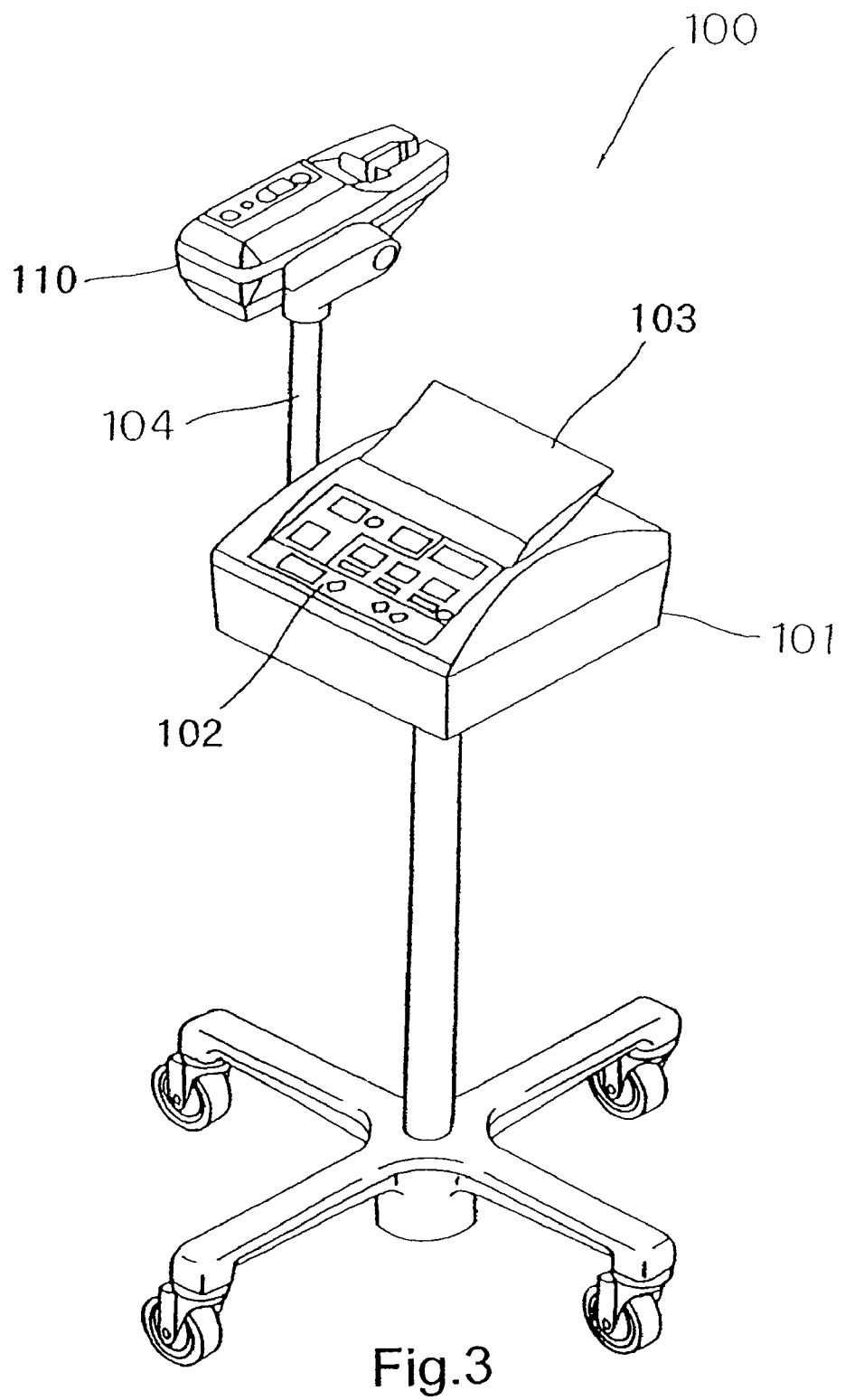
FIG. 3 is a perspective view illustrating the outer appearance of the liquid injector.
Figure 4A:
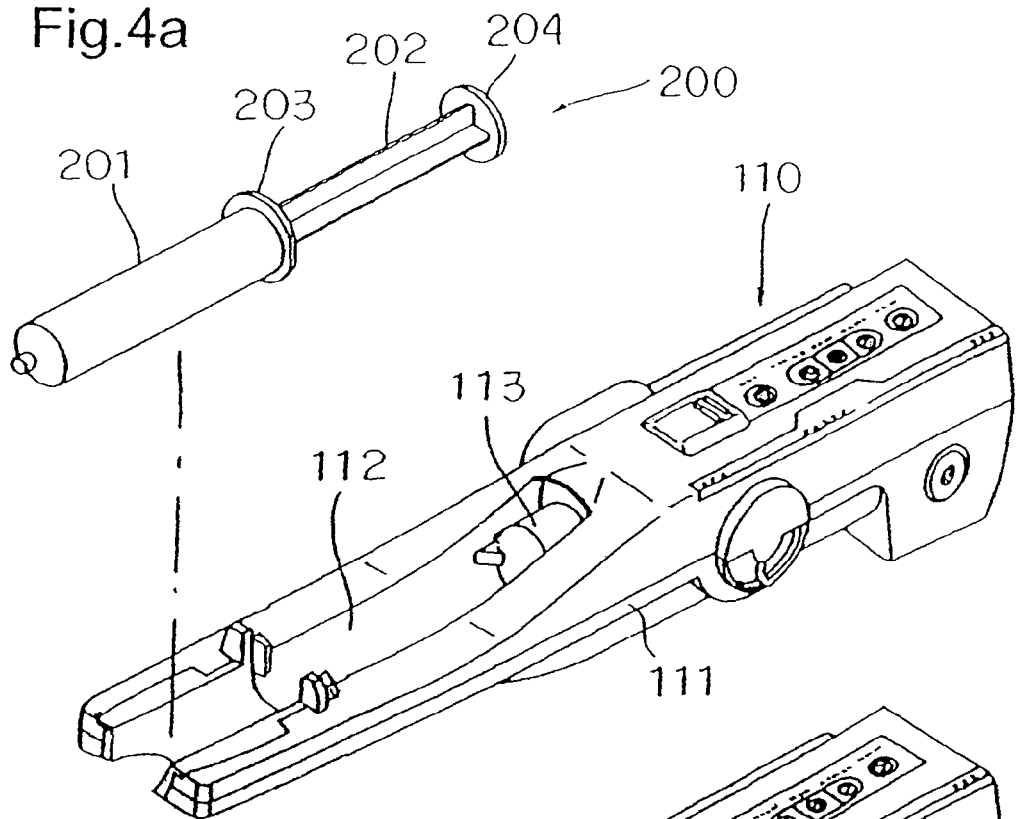
FIGS. 4a and 4b are perspective views illustrating how a liquid syringe is mounted on an injection head.
Figure 4B:
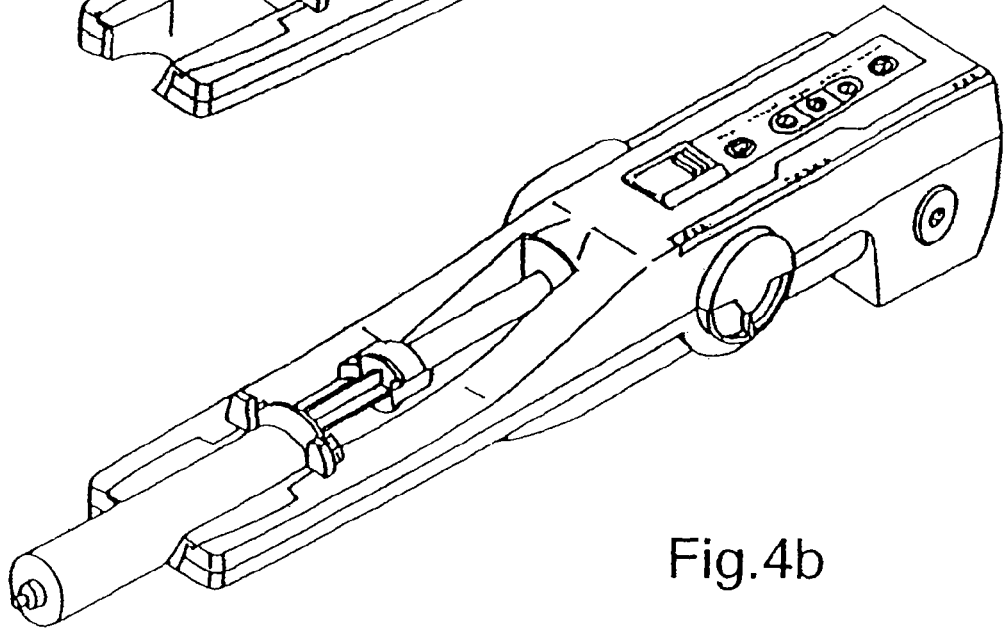

Referring to FIG. 3, liquid injector 100 of this embodiment comprises injector body 101; operation panel 102 and liquid crystal display 103 provided on the top surface of injector body 101; and injection head 110 supported by a movable arm 104 on one side of injector body 101. as shown in FIG. 4, injection head 110 is formed with recess 112 which has the shape of a semi-cylindrical groove, such that liquid syringe 200 is removably fitted in recess 112.

Liquid syringe 200 comprises cylinder member 201 and piston member 202, where piston member 202 is slidably inserted into cylinder member 201. Cylinder member 201 is formed with cylinder flange 203 around the outer periphery of the distal end thereof, while piston member 202 is formed with piston flange 204 around the outer periphery of the distal end thereof.

Figure 7:
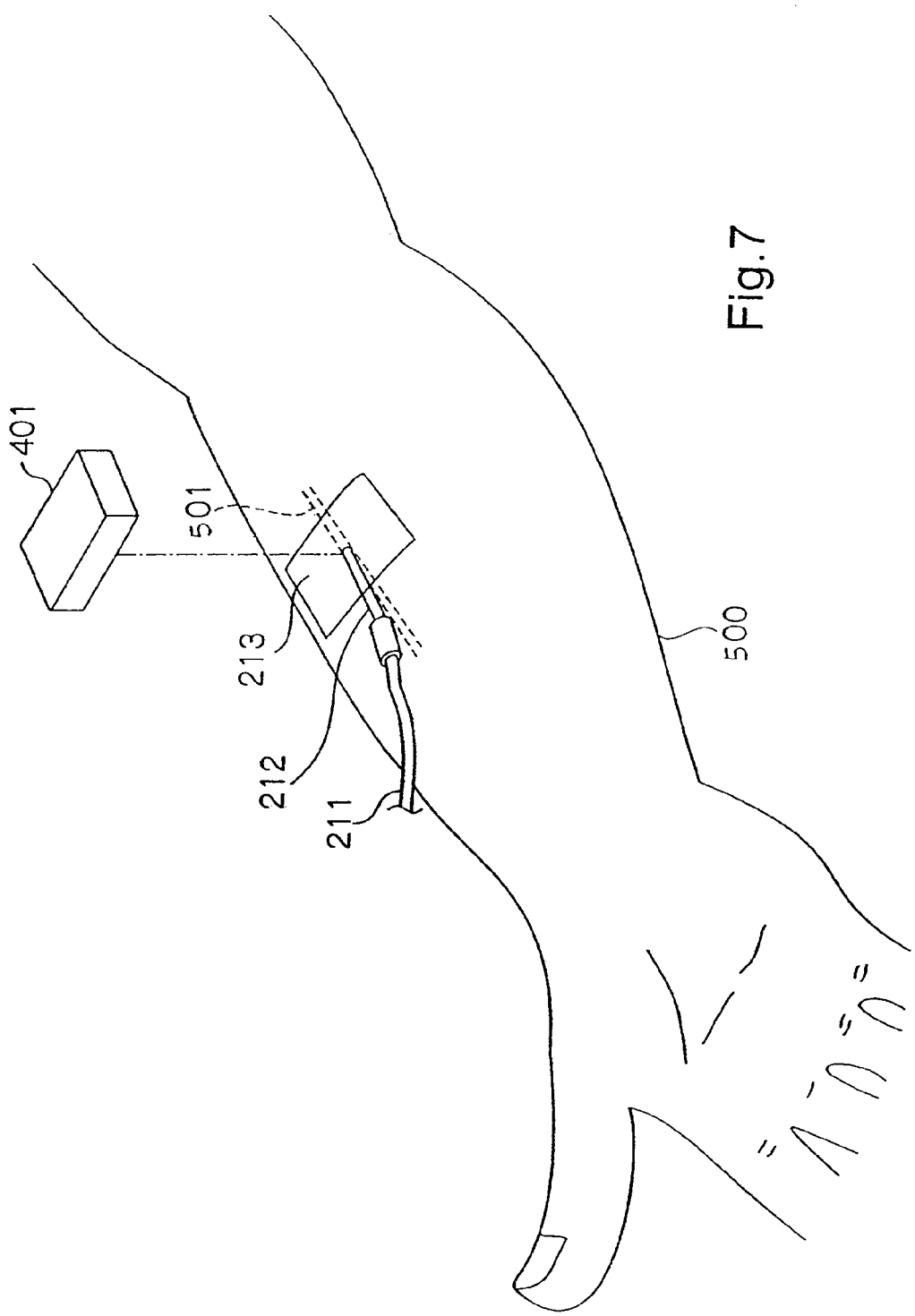
FIG. 7 is a perspective view illustrating how the leak detection unit is mounted on an arm of a human.

In liquid injector 100 of this embodiment, liquid cylinder 200 held in injection head 110 is coupled to blood vessel 501 in arm 500 of a human body through extension tube 211 and needle 212, and needle 212 is held by adhesive pad 213 made of a transparent sheet which is highly transparent to infrared rays, for example, as can be seen in FIG. 7.

Figure 2:
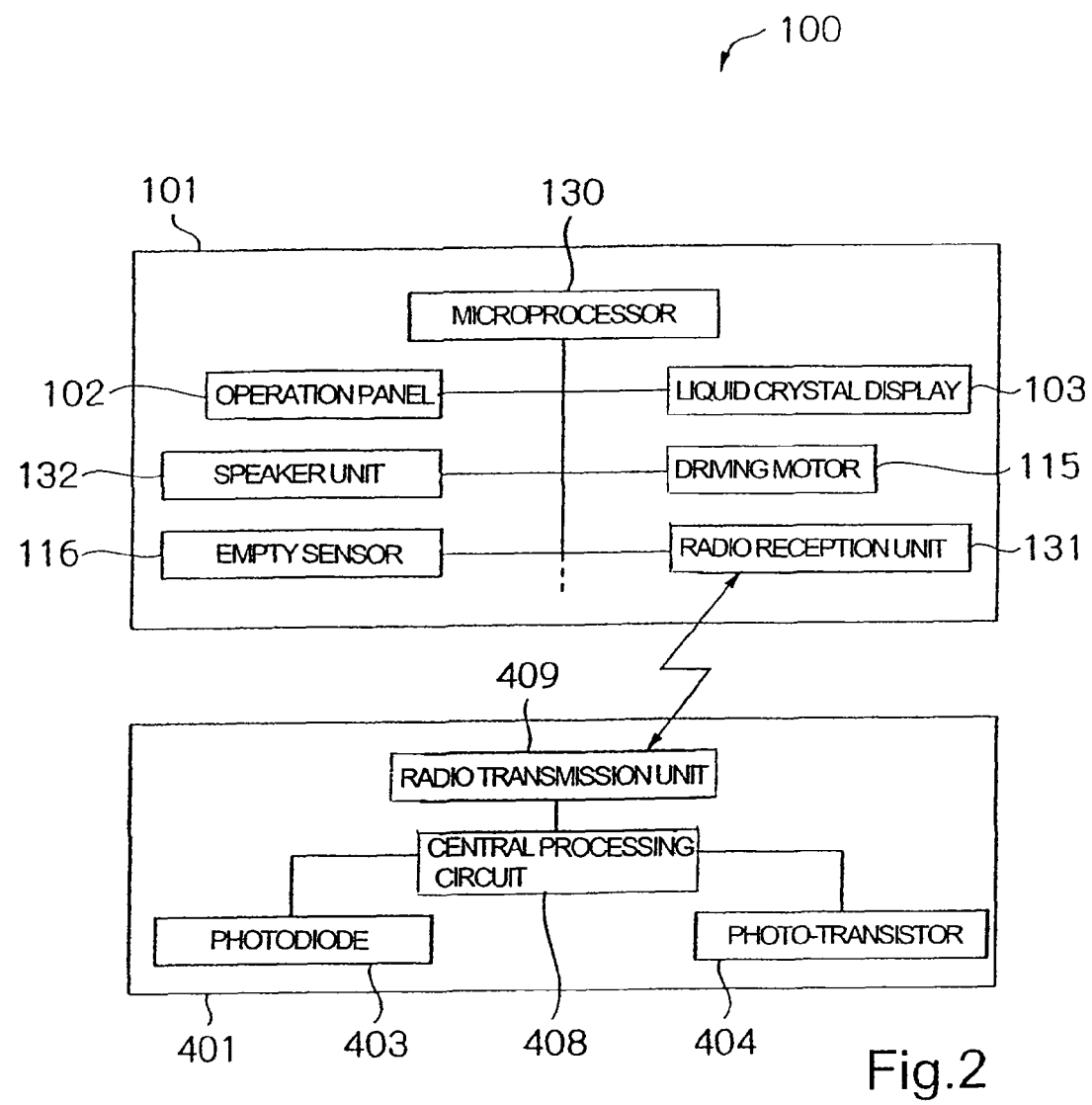
FIG. 2 is a block diagram illustrating the physical structure of the liquid injector.

Injection head 110 has piston driving mechanism 113 disposed behind recess 112 of syringe holder member 111 for holding and moving back-and-forth piston flange 204. Specifically, piston driving mechanism 113 contains driving motor 115 and empty sensor 116, as shown in FIG. 2, and actuates with driving motor 115 which acts as a power source. Empty sensor 116 in turn detects piston flange 204 at a particular position to sense that liquid syringe 200 has completely injected a liquid.

In this embodiment, liquid injector 100 is formed integrally with a leak detector, wherein injector body 101 also serves as a detector body. Thus, leak detection unit 401 is formed separately from injector body 101, and makes radio communications with injector body 101.

Figure 6:
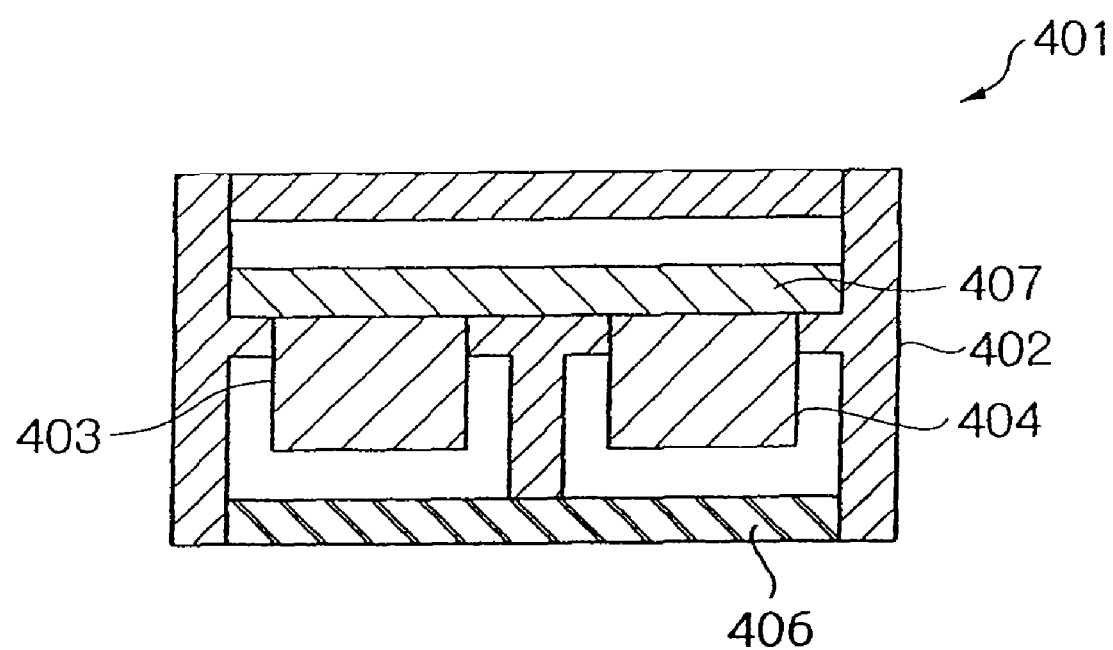
FIG. 6 is a front longitudinal sectional view illustrating a leak detection unit.

More specifically, leak detection unit 401 has a flat box-shaped unit housing 402, as shown in FIG. 7, and contains photodiode 403 which represents a pulse generating means, and photo-transistor 404 which represents a pulse detecting means within unit housing 402. Photodiode 403 and photo-transistor 404 are oriented downward in unit housing 402, as can be seen in FIG. 6.

Photodiode 403 emits infrared rays at a predetermined wavelength downward as wave propagation, while photo-transistor 404 receives the infrared rays at that wavelength from below. Optical filter 406, which passes therethrough only the infrared rays at the predetermined wavelength, is disposed at a position opposite to and below these photodiode/photo-transistor 403, 404. The infrared rays are set at a wavelength at which they transmit through particular organs of a human body, and are reflected by particular organs. For example, the infrared rays at the set wavelength are highly penetrative through skin and fat, but is highly reflective to muscles.

Circuit board 407 is disposed in an upper region within leak detection unit 401, and has mounted thereon photodiode/photo-transistor 403, 404, central processing circuit 408, and radio transmission unit 409, respectively.

Central processing circuit 408 is in wired connection with photodiode/photo-transistor 403, 404 as well as with radio transmission unit 409 for forcing photodiode 403 to sequentially emit pulse signals and for detecting the pulse signals from the output of photo-transistor 404.

Also, central processing circuit 408, which comprises logic circuits in a predetermined structure, has a variety of hardware components which function as interval measuring circuit 411, interval storing circuit 412, difference calculating circuit 413, and difference comparing circuit 414.

Interval measuring circuit 411, which comprises, for example, a counter circuit or the like, measures a time interval between emission and detection of each of the pulse signals.

Interval storing circuit 412, which comprises, for example, a FIFO (First In First Out) memory or the like, stores a measured time interval until the next time interval is measured.

Difference calculating circuit 413, which comprises, for example, a subtract circuit or the like, calculates the difference between the last measured time interval, as a reference time interval, and the currently measured time interval.

Difference comparing circuit 414, which comprises, for example, a comparator circuit or the like, compares the calculated difference with a predetermined acceptable range.

Then, when the difference does not exceed the acceptable range, central processing circuit 408 instructs radio transmission unit 409 to transmit a predetermined standby signal at all times through radiowaves. As the difference exceeds the acceptable range, central processing circuit 408 instructs radio transmission unit 409 to transmit a predetermined warning signal over the air.

Referring back to injector body 101, which contains microprocessor 130 as shown in FIG. 2, microprocessor 130 is in wired connection with operation panel 102, liquid crystal display 103, driving motor 115, empty sensor 116, radio reception unit 131, speaker unit 132, and the like.

Figure 1:
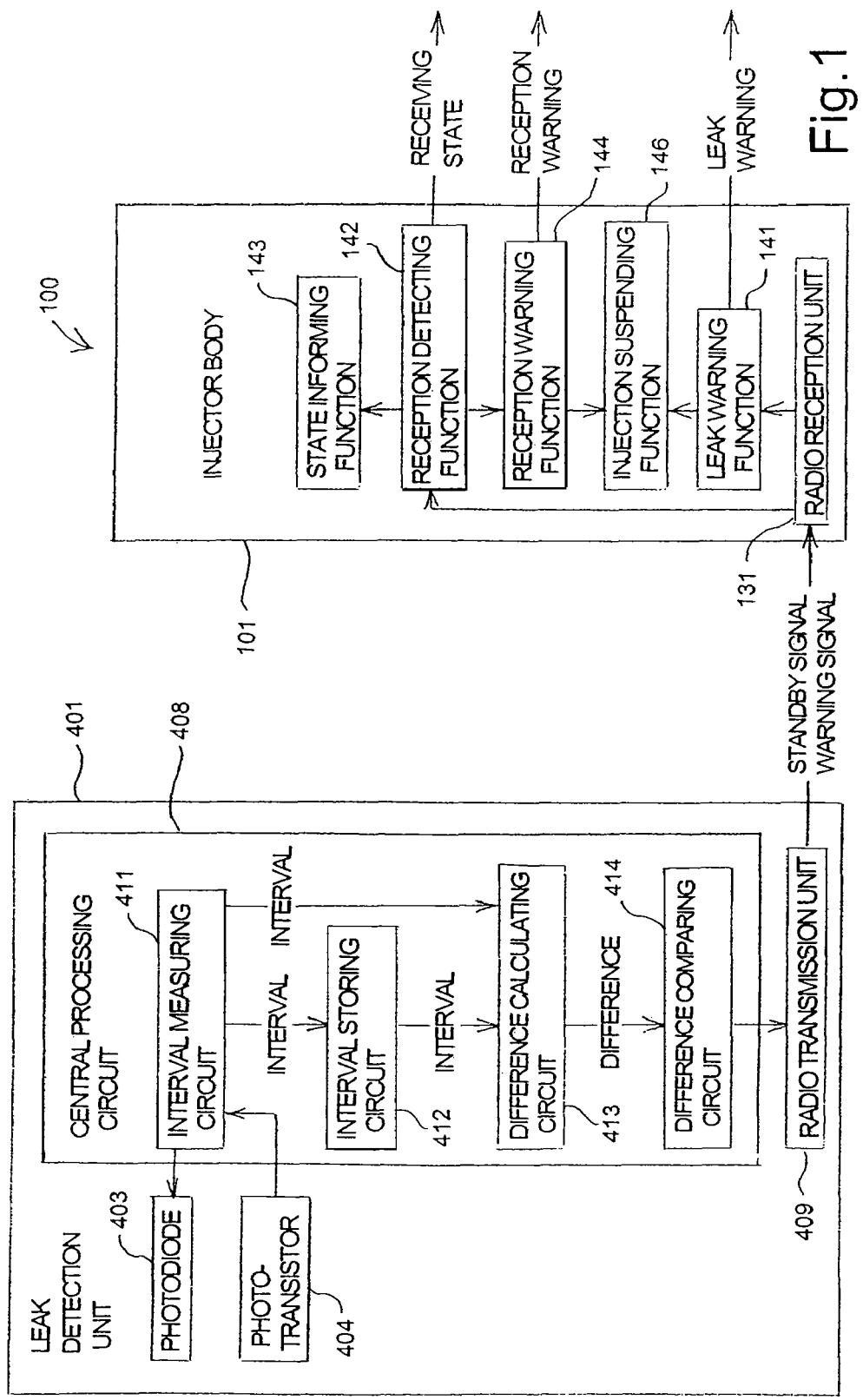
FIG. 1 is a schematic diagram illustrating the logical structure of a liquid injector according to one embodiment of the present invention.

Microprocessor 130, which comprises a so-called one-chip microcomputer, has appropriate computer programs installed in the form of firmware or the like. Microprocessor 130 totally controls the foregoing respective components in accordance with the computer programs, thus allowing liquid injector 100 of this embodiment to logically have a variety of functions including leak warning function 141, reception detecting function 142, state informing function 143, reception warning function 144, and injection suspending function 146, as shown in FIG. 1.

Leak warning function 141 represents a function of microprocessor 130 for controlling the operation of speaker unit 132 and liquid crystal display 103 in accordance with a computer program. Specifically, as a standby signal received by radio reception unit 131 over the air is switched to a warning signal, leak warning function 141 generates a leak warning audibly from speaker unit 132 and visually from liquid crystal display 103 for notification to the operator.

Reception detecting function 142 represents a function of microprocessor 130 for detecting the operating state of radio reception unit 131. Specifically, microprocessor 130 detects the receiving state of radio signals. State informing function 143 represents a function of microprocessor 130 for controlling the operation of liquid crystal display 103. Specifically, microprocessor 130 informs a receiving state detected by reception detecting function 142 in the form of an image displayed on liquid crystal display 103.

Reception warning function 144 also represents a function of microprocessor 130 for controlling the operation of speaker unit 132 and liquid crystal display 103. Specifically, as the receiving state detected by reception detecting function 142 falls below a predetermined state, microprocessor 130 generates a reception warning audibly from speaker unit 132 and visually on liquid crystal display 103 for notification to the operator.

Injection suspending function 146 represents a function of microprocessor 130 for controlling the operation of driving motor 115 of piston driving mechanism 113. Specifically, microprocessor 130, responsive to at least one of a leak warning and a reception warning, stops driving motor 115 to suspend the injection of a liquid.

A variety of foregoing functions 141-146 of liquid injector 100 as mentioned above are implemented using hardware such as speaker unit 132 and the like as required, but are essentially implemented by microprocessor 130 which runs in accordance with computer programs installed therein.

Such computer programs are described to cause microprocessor 130 to execute processing operations, for example, instructing speaker unit 132 and liquid crystal display 103 to generate a leak warning for notification in response to a warning signal received by radio reception unit 131 over the air; instructing driving motor 115 in association with the generation of the leak warning; detecting the receiving state of radio reception unit 131; displaying the receiving state on liquid crystal display 103 for notification; instructing speaker unit 132 and liquid crystal display 103 to generate a reception warning for notification in response to the receiving state falling below a predetermined state; stopping driving motor 115 in association with the generation of the reception warning, and so on.

Figure 5:
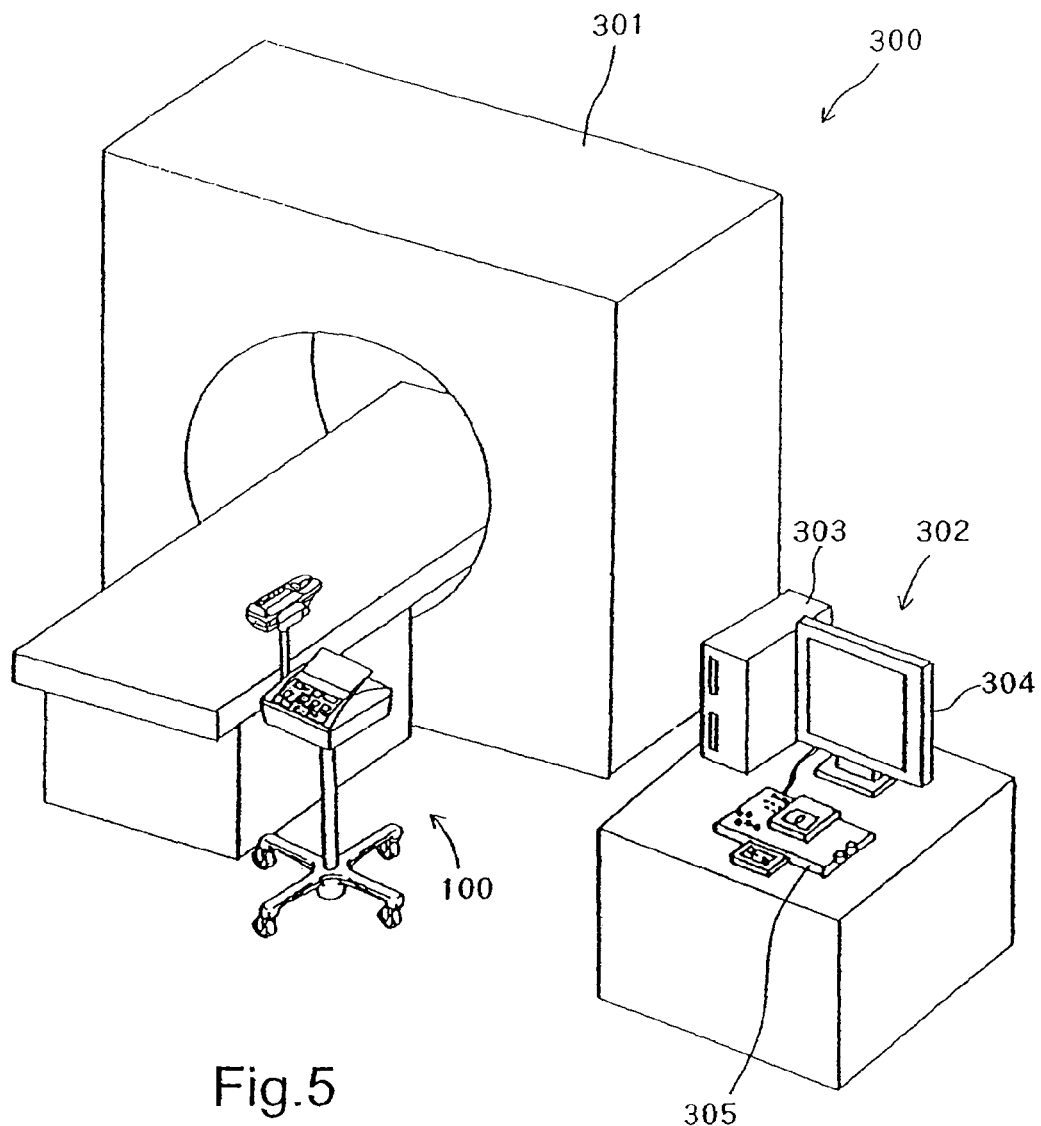
FIG. 5 is a perspective view illustrating the outer appearance of an MRI apparatus.

As illustrated in FIG. 5, liquid injector 100 of this embodiment is used, for example, near imager unit 301 of MRI apparatus 300, and may be connected to control unit 302 of MRI apparatus 300 as required. Control unit 302, which comprises a computer system that has detector body 303, liquid crystal display 304, and keyboard 305, controls the operation of imager unit 301, and displays a tomographic image on liquid crystal display 304.

For simplifying the illustration in FIG. 5, both liquid injector 100 and control unit 302 are positioned near imager unit 301, whereas in an actual medical field, liquid injector 100 alone is typically disposed near imager unit 301, with control unit 302 being installed in a different room.

Operation of Embodiment

In the configuration as described above, when liquid injector 100 of this embodiment is used, for example, the operator couples needle 212 through extension tube 211 to liquid syringe 200 filled with a liquid such as a contrast agent, and inserts needle 212 into blood vessel 501 in arm 500 of a patient positioned in imager unit 301 of MRI apparatus 300, as shown in FIG. 7, using adhesive pad 213 for holding needle 212 on arm 500.

Next, leak detection unit 401 is mounted on adhesive pad 213 with a binding belt (not shown), and liquid syringe 200 is loaded into injection head 10 of liquid injector 100. In such a state, leak detection unit 401 and injector body 101 are each powered on, followed by a predetermined manipulation to set injector body 101 into an operation mode for using leak detection unit 401.

Figure 8:
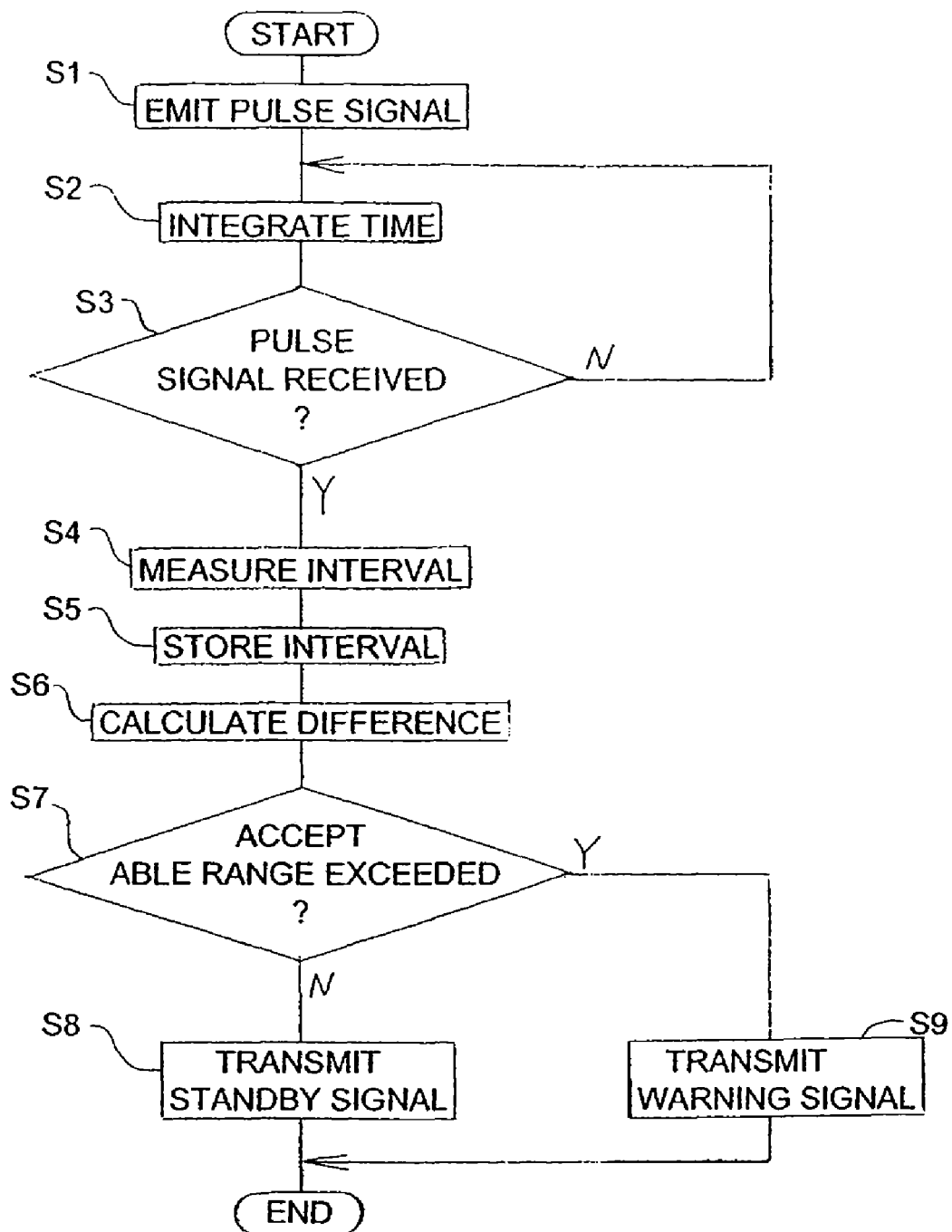
FIG. 8 is a flow chart illustrating the processing operation of the leak detection unit.

In response, leak detection unit 401 sequentially emits infrared pulse signals from photodiode 403 toward a position of arm 500 at which needle 212 is coupled (step S1), as shown in FIG. 8. However, as shown in FIG. 11, the infrared pulse signals are highly penetrative through particular organs of human and are highly reflective to other particular organs, thus permitting photo-transistor 404 to detect such reflected pulse signals (step S3).

In this event, a time interval is measured between the emission and the detection of each pulse (steps S1-S4), and the measured interval is held (step S5). Simultaneously, the last measured interval is referenced to calculate the difference between the currently measured interval and the last measured interval (step S6), followed by a determination which is made as to whether or not the difference exceeds an acceptable range (step S7).

Then, leak detection unit 401 transmits a standby signal indicative of "normal" to injector body 101 over the air if the difference does not exceed the acceptable range (step S8), and transmits a warning signal indicative of "anomalous" if the difference exceeds the acceptable range (step S9).

For example, if needle 212 becomes detached from blood vessel 501 in arm 500, into which it has been inserted, as shown in FIG. 7, a liquid will not be injected into blood vessel 501 but into its surroundings to swell arm 500 out, as can be seen on the surface of the skin as shown in FIG. 11b. Consequently, the pulse signal emitted from photodiode 403 is reflected within swelling arm 500, causing a path to extend until the pulse signal is detected by photo-transistor 404, as appreciated from FIGS. 11a and 11b.

In this event, since the measured interval between the reflection and the detection for the pulse signal is increased, this increase is calculated as the difference between the last and currently measured intervals. As this difference exceeding the predetermined acceptable range will cause radio transmission unit 409 to transmit the warning signal over the air, the swelling skin surface results in radio transmission of the warning signal.

Figure 9:
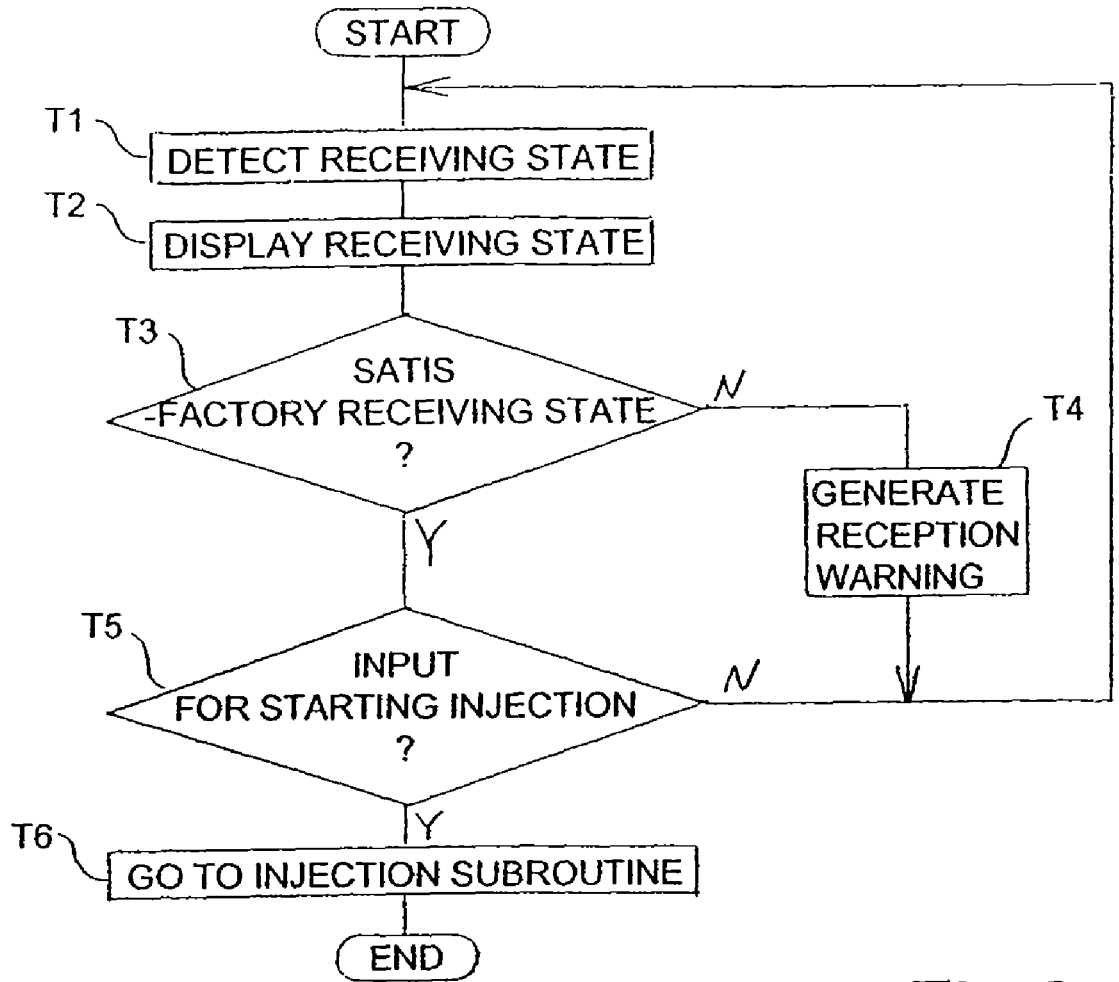
FIG. 9 is a flow chart illustrating a main routine of the processing operation of an injector body.
Figure 10:
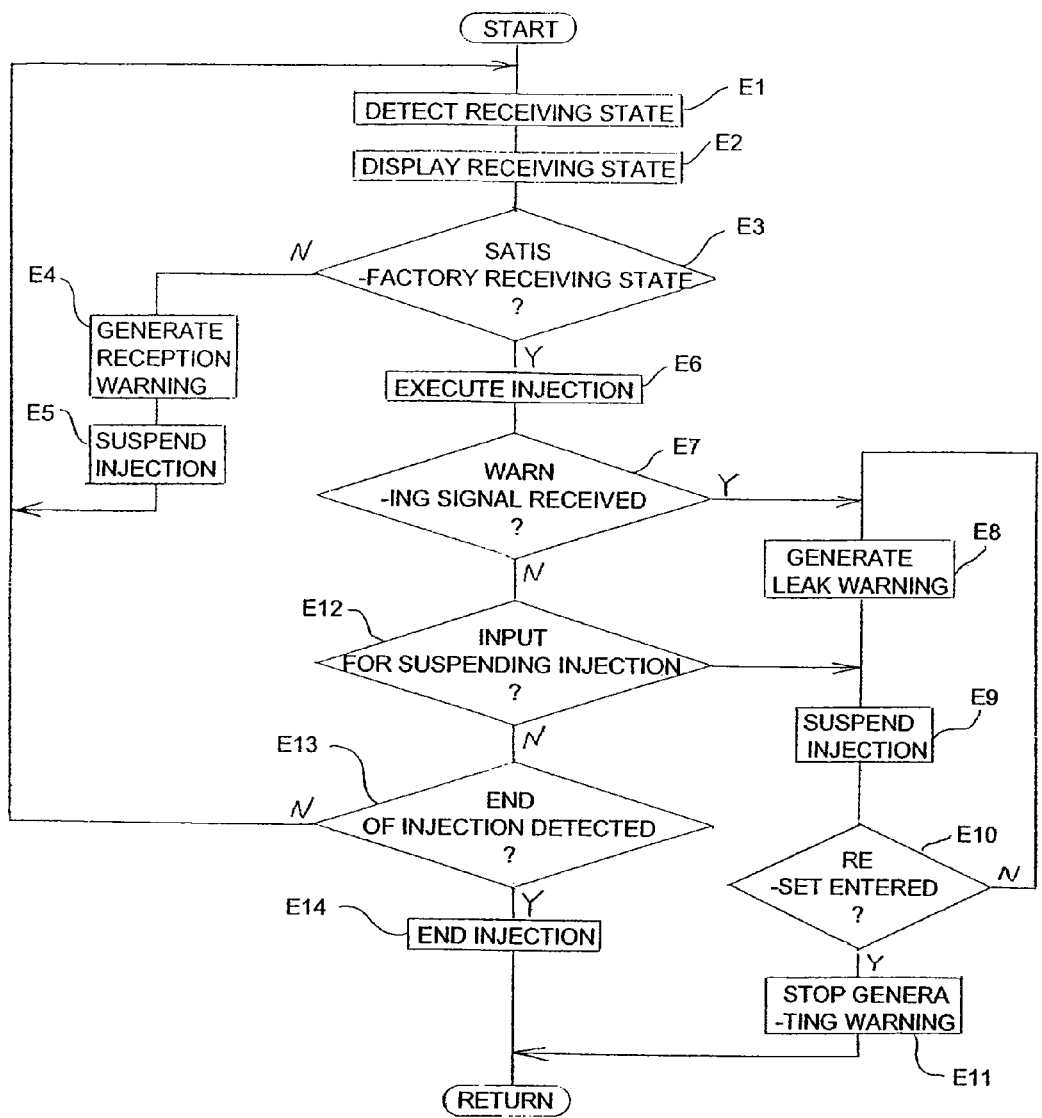
FIG. 10 is a flow chart illustrating a subroutine of an injection process.

When injector body 101 is operating using leak detection unit 401, injector body 101 detects the receiving state of the radiowaves at all times (step T1), and displays the receiving state on liquid crystal display 103 in the form of bar graph or the like in real time (step T2), as shown in FIG. 9.

With the foregoing operation, the operator can confirm the receiving state of the radiowaves from leak detection unit 401 in real time while operating injector body 101, and will adjust the position of injector body 101 and leak detection unit 401 if the receiving state is not proper.

Also, as the receiving state detected as mentioned above falls below the predetermined state (step T3), injector body 101 displays a reception warning such as "RADIOWAVES CANNOT BE RECEIVED. CONFIRM COMMUNICATION STATE." on liquid crystal display 103, and audibly generates the reception warning from speaker unit 132 (step T4).

In this event, since injector body 101 does not accept any input operation for resuming the injection until the receiving state from leak detection unit 401 ameliorates (steps T3-T5), injector body 101 does not start the liquid injecting operation unless a proper receiving state is recovered (step T6).

Further, when injector body 101 accepts an input operation for starting the injection of a liquid (steps T5, T6), injector body 101 still detects the receiving state of radiowaves at all times for display on liquid crystal display 103 in real time (steps E1, E2).

Then, as the detected receiving state falls below the predetermined state, injector body 101 generates a reception warning visually from liquid crystal display 103 and audibly from speaker unit 132 for notification to the operator (steps E3, E4), and does not perform the liquid injecting operation unless the receiving state is determined as proper.

When the injecting operation is in progress with a proper receiving state (step E6), injector body 101 is responsive to a change from the standby signal, received thereby over the air, to a warning signal (step E7) so as to display a leak warning such as "NEEDLE IS DETECTED TO COME OFF. CONFIRM NEEDLE" on liquid crystal display 103, and to audibly generate the leak warning from speaker unit 132 (step E8).

In this event, since the liquid injecting operation is suspended (step E9), the liquid will not be continuously injected while needle 212 remains off blood vessel 501. Further, since the leak warning is continuously generated for notification until a predetermine reset operation is performed on injector body 101 (steps E10, E11), the operator will confirm the leak warning without overlooking it.

In liquid injector 100 of this embodiment, as the operator, who has confirmed the leak warning, appropriately inserts needle 212 into blood vessel 501 and then operates on operation panel 102 to start injecting the liquid, liquid injector 100 can resume injecting the liquid in response to the operation (steps T5, T6).

Also, when the operator operates on operation panel 102 to suspend the injection (step E12), injector body 101 likewise suspends the injection of the liquid (step E9). Further, when empty sensor 116 detects that the injection of the liquid is completed (step E13), injector body 101 finishes the injection of the liquid (step E14).

Effects of Embodiment

Liquid injector 100 of the foregoing embodiment sequentially emits infrared pulse signals toward a position of arm 500 at which needle 212 is inserted, and detects those pulse signals which are reflected within arm 500, as described above. Then, liquid injector 100 calculates the difference between a time interval between the emission and the detection, measured for each pulse signal, and a reference time interval, and generates a leak warning for notification if the difference exceeds a predetermined acceptable range.

With the foregoing approach, when needle 212 becomes detached from blood vessel 501 to leak or extravasation a liquid which causes arm 500 of the human body to swell out on the surface, liquid injector 100 generates a leak warning, thereby permitting the operator to immediately recognize that needle 212 has come off blood vessel 501 of the patient for taking appropriate actions thereto.

Moreover, upon detection of needle 212 which has come off blood vessel 501, liquid injector 100 of this embodiment automatically suspends the injection of the liquid, making it possible to automatically prevent the liquid from being continuously injected with needle 212 remaining off blood vessel 501.

Further, as described above, since liquid injector 100 of this embodiment relies on a swelling recognized on a skin surface to detect that needle 212 has come off blood vessel 501, and relies on a change in the path length of infrared rays reflected from a human organ to detect the swelling on the skin surface, liquid injector 100 can detect a leaking liquid in a simple structure without substantially suffering from a degraded accuracy due to disturbance.

Furthermore, liquid injector 100 of this embodiment stores a time interval measured between the emission and the detection of each pulse at least until the next measurement, and calculates the difference between the currently measured interval and the last measured interval which is used as a reference time interval. This way of calculating the difference eliminates the need for previously setting an appropriate reference time interval, enabling liquid injector to successfully detect a change in position of a skin surface irrespective of whichever site of human body to be monitored, personal differences in skinfold thickness, and the like.

Further, since photodiode 403 emits infrared pulse signals at a wavelength which transmit through particular organs in arm 500 of the human body and are reflected by other particular organs, the pulse signals can be made to transmit through the surface of the human body and to be reflected from a particular organ. Moreover, since optical filter 406 passes the infrared rays only at that wavelength therethrough to photo-transistor 404, it is possible to prevent photo-transistor 404 from erroneously detecting surrounding light noise.

Further, liquid injector 100 of this embodiment comprises leak detection unit 401 which contains photodiode 403, photo-transistor 404, radio transmission unit 409, and the like separately from injector body 101 which contains radio reception unit 131, liquid crystal display 103, speaker unit 132, and the like.

Then, as leak detection unit 401 detects a swelling on a skin, injector body 101 generates a leak warning for notification through radio communication, leak detection unit 401, which is mounted directly on a human body, can be reduced in size and weight for facilitating its handling. Even with such a smaller and lighter configuration, leak detection unit 401 can ensure that a leak warning is recognized by the operator who is manually operating injector body 101 remotely from leak detection unit 401.

Moreover, injector body 101 detects at all times a receiving state of a radio signal from leak detection unit 401 to inform the receiving state in real time. This permits the operator to recognize at all times a communicating state between leak detection unit 401 and injector body 101, and to take an appropriate action to an improper communicating state, if any, before the injection is started.

Further, since injector body 101 generates a reception warning for notification if a detected receiving state falls below a predetermined state, liquid injector 100 can prevent a failure in receiving the warning signal due to a faulty communication, and a resulting failure in generating the leak warning. In addition, since liquid injector 100 suspends the liquid injection if even one of the leak warning and reception warning is generated for notification, liquid injector 100 can not only automatically prevent a liquid from being continuously injected while needle 212 remains off blood vessel 501 but also prevent the liquid from being continuously injected while it remains incapable of receiving the warning signal over the air.

Exemplary Modifications to Embodiment

It should be understood that the present invention is not limited to the foregoing embodiment but may be modified in various ways without departing from the spirit and scope of the invention. For example, while the foregoing embodiment has illustrated liquid injector 100 integrated with leak detection unit 401, leak detection unit 401 may be formed separately from liquid injector 100.

Nevertheless, liquid injector 100 is advantageously integrated with leak detection unit 401 because the injection of a liquid must be immediately suspended upon detection of a leak or an extravasation of the liquid, as described above. Therefore, when leak detection unit 401 is formed separately from liquid injector 100, liquid injector 100 is preferably configured to suspend the injection in response to a warning generated by leak detection unit 401.

Further, while the foregoing embodiment has illustrated that liquid injector 100 generates a leak warning and a reception warning for notification, such warnings may be transmitted to control unit 302 of MRI apparatus 300 to display the warnings on liquid crystal display 304 for visual notification. As previously described, since control unit 302 is installed at a location remote from imager unit 301, the warnings are beneficially communicated to imager unit 301.

Also, while the foregoing embodiment has illustrated that liquid injector 100 suspends the injection in response to a leak warning, MRI apparatus 300 can also stop imaging in association with such a suspended operation of liquid injector 100. In this event, liquid injector 100 can transmit the warning signal from leak detection unit 401 directly to MRI apparatus 300, or alternatively can transmit the warning signal indirectly from injector body 101.

While the foregoing embodiment has been illustrated on the assumption that liquid injector 100 is used near MRI apparatus 300, liquid injector 100 may be used near a CT scanner, a PET apparatus, an angio apparatus, an MRA apparatus, an ultrasonic diagnosis apparatus, and so on.

Further, while the foregoing embodiment has illustrated that leak detection unit 401 makes radio communications with injector body 101 through radiowave signals, liquid injector 100 can employ any communication scheme, including an ultrasonic signal based wireless communication, an optical signal based wireless communication, an electric signal based wired communication, an optical signal based wired communication, and so on.

Also, while the foregoing embodiment has illustrated that leak detection unit 401 emits infrared pulse signals to a human body, detects those infrared pulse signals reflected from the human body, and calculates the difference between a measured time interval between the emission and the detection for each pulse signal and a reference time interval which is the last measured interval, the first measured interval may be defined as the reference interval.

Further, the foregoing embodiment has illustrated that the infrared pulse signals transmit through particular organs of a human body and are reflected by other particular organs, so that leak detection unit 401 detects that needle 212 has come off blood vessel 501, taking advantage of the fact that a swelling skin surface due to a leaking liquid causes a change in time interval between the emission and the detection of the infrared pulse signal.

However, when the infrared rays transmit through particular organs of a human body and are reflected by other particular organs, a liquid leaking into one of the reflective organs causes a change in wavelength of the reflected infrared rays. Bearing this in mind, leak detection unit 401 can detect that needle 212 has come off blood vessel 501 by measuring the wavelength of detected infrared rays, and comparing the measured wavelength with a predetermined reference wavelength. In this event, the last measured wavelength may be used likewise as a reference wavelength, or the first measured wavelength may be used as the reference wavelength.

Also, while the foregoing embodiment has illustrated that photodiode 403 is used as a pulse generating means for generating infrared pulse signals, and photo-transistor 404 is used as a pulse detecting means for detecting the infrared pulse signals, photodiode 403 may be replaced, for example, with an ultrasonic vibrator (not shown) for transmitting ultrasonic pulse signals for use as the pulse generating means, and photo-transistor 404 may be replaced with an ultrasonic detector device (not shown) for detecting ultrasonic pulse signals for use as the pulse detecting means. Since the resulting leak detector (not shown) can ultrasonically detect a leak or an extravasation of a liquid, it is not affected by surrounding light rays in the detection.

Figure 12A:
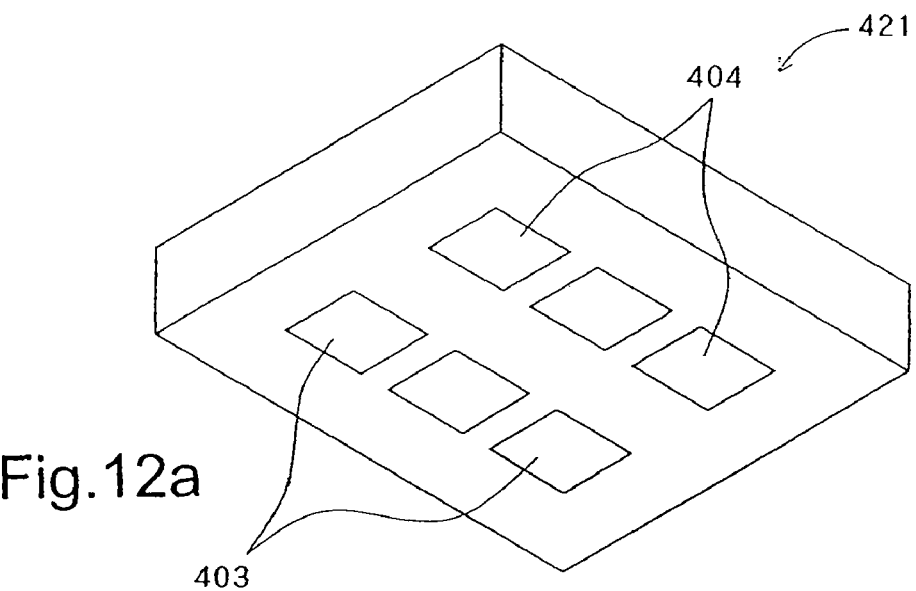
FIGS. 12a and 12b are perspective views each illustrating an exemplary modification to the leak detection unit.
Figure 12B:
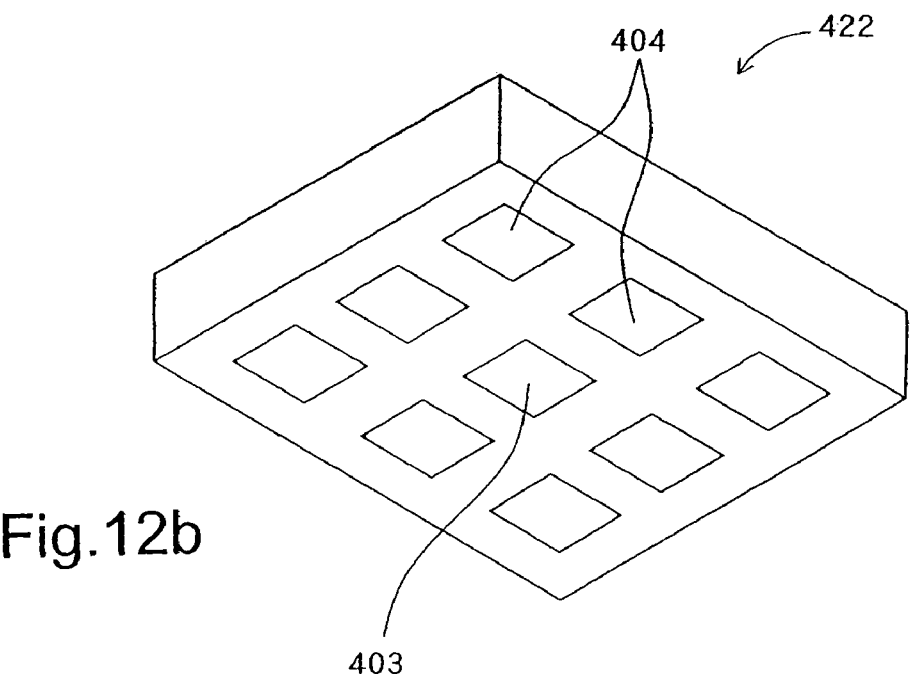

Further, while the foregoing embodiment has illustrated that leak detection unit 401 is mounted with one each of photodiode 403 and photo-transistor 404, leak detection unit 401 may be replaced with leak detection unit 421 having a plurality of photodiodes 403 and a plurality of photo-transistors 404 arranged in matrix as shown in FIG. 12a, or with leak detection unit 422 having a plurality of photo-transistor 404 arranged around single photodiode 403 as shown in FIG. 12b. Since the resulting leak detector can detect a leaking liquid at a plurality of sites, it can detect a leaking liquid at an exact site.

Also, while the foregoing embodiment has shown adhesive pad 213 made of a simple transparent sheet for holding needle 212 and for adhering leak detection unit 401 on arm 500, adhesive pad 221 made of a transparent sheet may be provided with printed marks 222, 223 for representing the positions of needle 212 and leak detection unit 401.

In this event, needle 212 and leak detection unit 401 can be placed in an appropriate positional relationship by aligning needle 212 and leak detection unit 401 to respective associated printed marks 222, 223 on adhesive pad 221, permitting leak detection unit 401 to readily detect a leaking liquid without fail.

Figure 14:
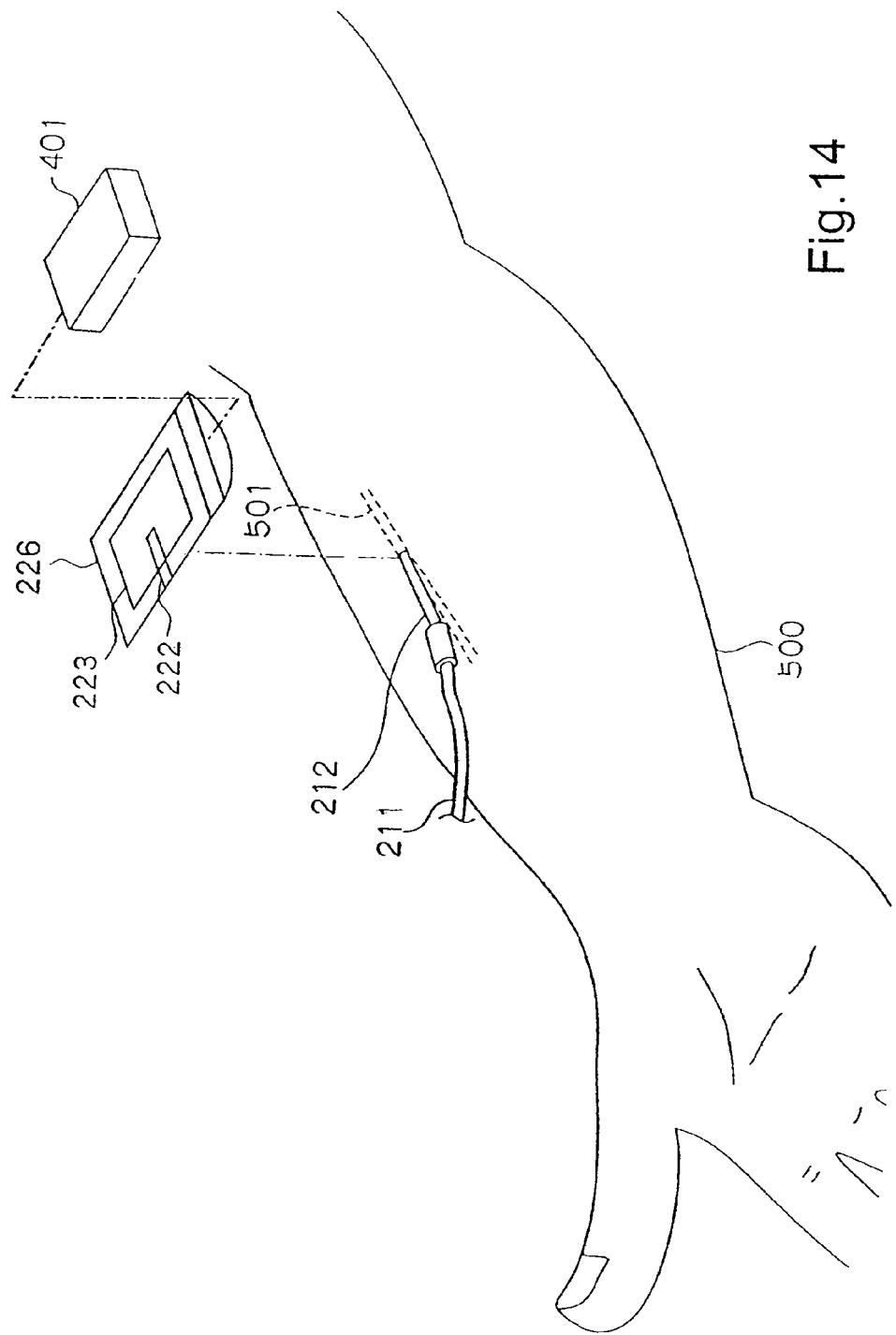
FIG. 14 is a perspective view illustrating how the leak detection unit is mounted onto an arm using another modified adhesive pad.

Optionally, as shown in FIG. 14, adhesive pad 226 may be formed in a bag shape to serve as a protection member, such that leak detection unit 401 can be enclosed in adhesive pad 226. In this event, since leak detection unit 401 can be prevented from damages and contaminations by adhesive pad 226 which is a replaceable consumable item, leak detection unit 401 can be readily disinfected.

Figure 15:
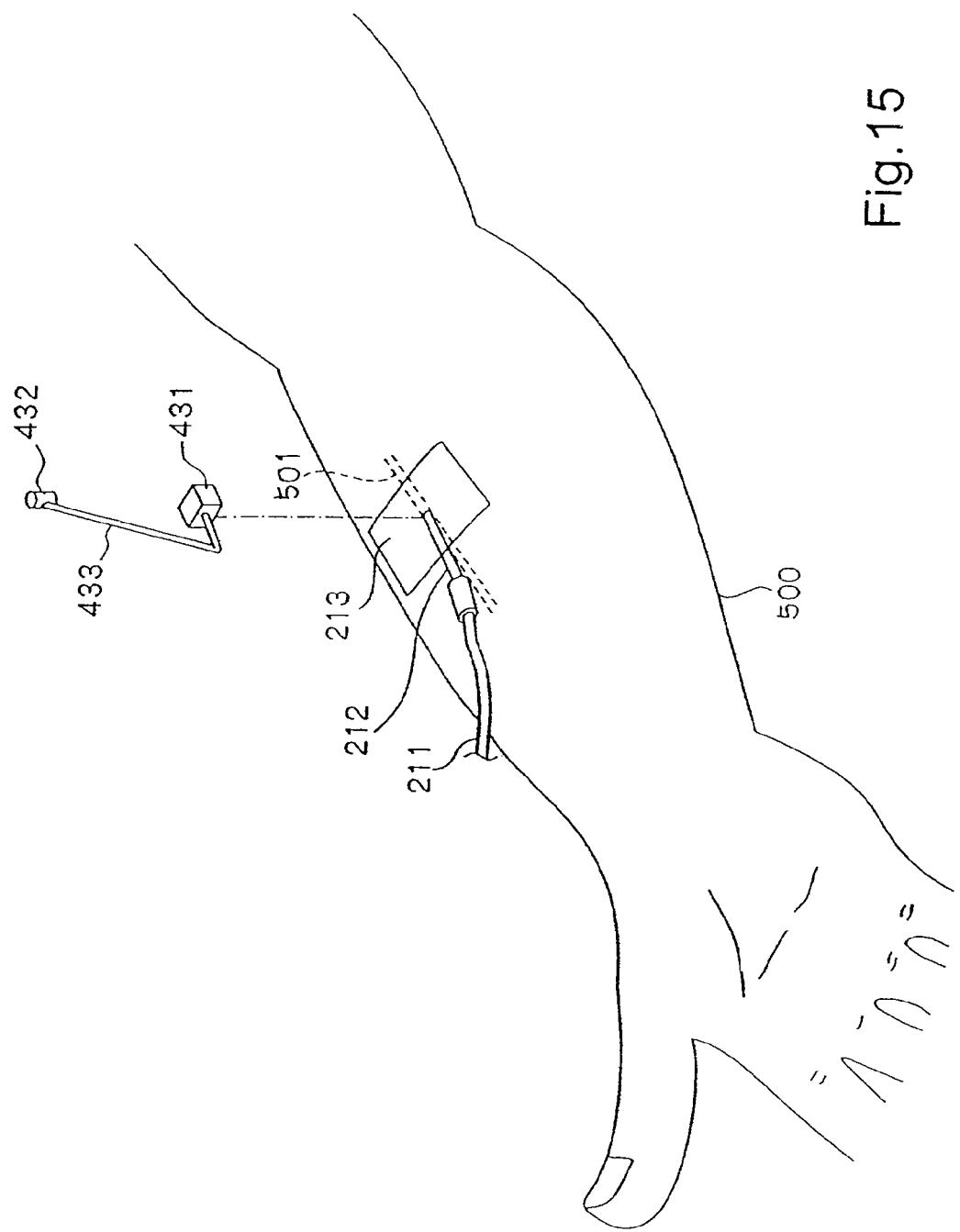
FIG. 15 is a perspective view illustrating another exemplary modification to the leak detection unit.

Also, as shown in FIG. 15, leak detection unit 431 may be formed to be sufficiently small, with CCD (Charge Coupled Device) camera 432 supported by an arm 433 above leak detection unit 431 for use as an imaging means. In this configuration, since CCD camera 432 captures an image around leak detection unit 431, the captured image is wirelessly transmitted to liquid injector 100 for display on liquid crystal display 103.

With the foregoing approach, the operator, who manipulates liquid injector 100, can also confirm the image around leak detection unit 431 on liquid crystal display 103 when a leak warning is displayed on liquid crystal display 103. Optionally, such an image may not be displayed at all times, but displayed only upon detection of a leaking liquid.

Further, while the foregoing embodiment has illustrated that liquid injector 100 drives leak warning function 141 to notify a leak warning alone through image display on liquid crystal display 103, liquid injector 100 can optionally display a measured time interval for each pulse signal in a trend graph representation by a graph display means (not shown) through image display on liquid crystal display 103.

Figure 16:
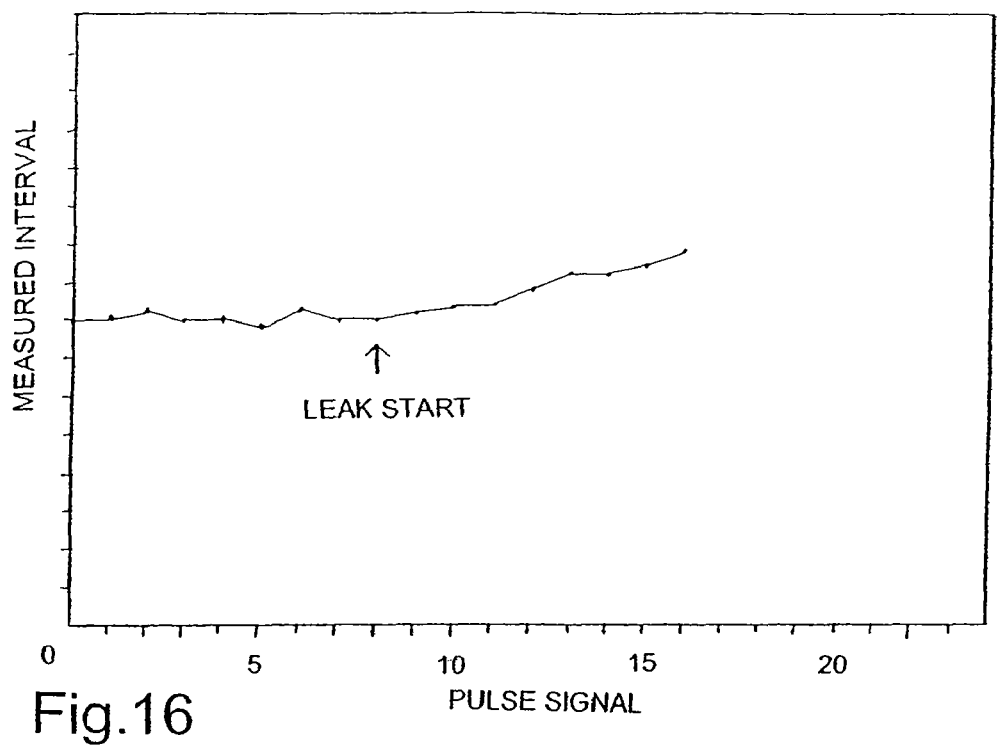
FIG. 16 is a schematic front view illustrating a display screen which displays a trend graph representing time intervals measured for respective pulse signals.

Since liquid injector 100 of the foregoing embodiment determines a leaking liquid when the difference between the last measured interval and the currently measured interval exceeds an acceptable range, liquid injector 100 may fail to determine a leaking liquid if the liquid leaks at an extremely low rate so that there is an imperceptible difference between the last and currently measured intervals, as shown in FIG. 16.

However, when the measured interval is represented by a trend graph displayed on liquid crystal display 103 as illustrated, the trend graph enables the operator to determine even a slow leak of a liquid.

Figure 17:
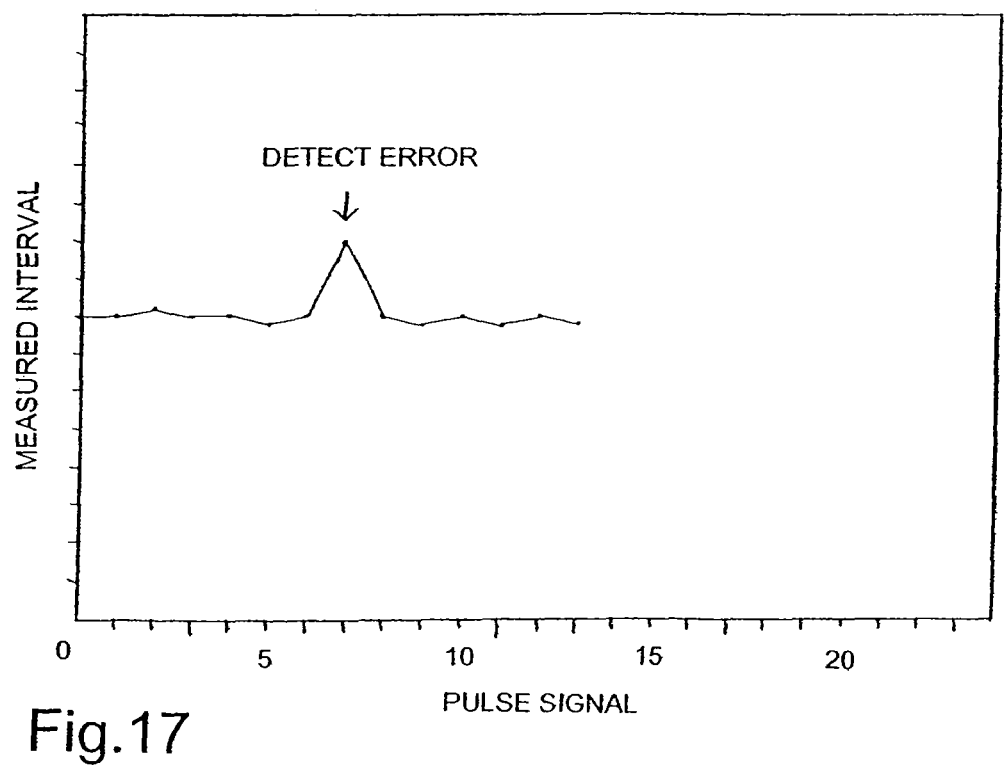
FIG. 17 is a schematic front view illustrating a display screen which displays a trend graph representing time intervals measured for respective pulse signals.

Also, liquid injector 100 of the foregoing embodiment may experience a temporary erroneous detection even if the difference between the last measured interval and the currently measured interval exceeds the acceptable range as shown in FIG. 17. However, the trend graph may be displayed as illustrated, permitting the operator to confirm even a temporary erroneous detection of a leaking liquid.

When liquid injector 100 detects the difference between wavelengths of pulse signals instead of the difference between measured intervals as described above, liquid injector 100 can likewise display the measured wavelengths as represented by a trend graph, and can also display the difference calculated from the measured intervals or measured wavelengths as represented by a trend graph (neither shown).

Further, while the foregoing embodiment has illustrated that upon detection of a leaking liquid, liquid injector 100 stops piston driving mechanism 113 to suspend the injection of a liquid, leak detection unit 401 may comprise an independent tube blocking mechanism (not shown) for blocking extension tube 211 upon detection of a leaking liquid.

Such a tube blocking mechanism may be formed, for example, in an independent modular structure mounted on extension tube 221 for making wireless or wired communications with leak detection unit 401 and/or detector body 101. The tube blocking mechanism may further has a feature for opening/closing extension tube 211 with a driving source such as a solenoid which blocks extension tube 211 upon detection of a leaking liquid.

Since such a leak detector independently blocks extension tube 211 upon detection of a leaking liquid, liquid injector 100 can automatically suspend the injection of a liquid even if it is not associated with the leak detector.

Also, while the foregoing embodiment has illustrated that microprocessor 130 functions in accordance with a computer program installed therein to logically implement a variety of functions 141-146 of injector body 101, at least some of various functions 141-144 may be formed in hardware such as dedicated logic circuits.

Conversely, while the foregoing embodiment has illustrated that a variety of circuits 411-414 in leak detection unit 401 are formed in given hardware, the functions of circuits 411-414 may be logically implemented, for example, by a microprocessor which runs in accordance with a computer program installed therein.

Further, while the foregoing embodiment has illustrated that one liquid syringe 200 is fitted in one recess 112 of liquid injector 100, a plurality of liquid syringes 200 may be fitted in a plurality of recesses of an injection head (not shown).

Also, the foregoing embodiment has illustrated that liquid syringe 200 is directly fitted in liquid injector 100. However, since liquid syringes 200 in a variety of sizes are commercially available at present, liquid syringe 200 of the largest size, for example, may only be fitted directly in liquid injector 100, while liquid syringes 200 of various size except for the largest one may be fitted in liquid injector 100 through respective dedicated cylinder adaptors (not shown).

The invention claimed is:

1. A leak detector for detecting a leak of a liquid injected through a needle into a blood vessel near the surface of a human body, comprising pulse generating means for sequentially emitting pulse signals toward said human body at a position at which said needle is inserted through wave propagation at a predetermined wavelength; pulse detecting means for detecting said pulses reflected inside of said human body; wavelength measuring means for measuring a wavelength for each of said detected pulse signals; difference calculating means for calculating the difference between the measured wavelength and a predetermined reference wavelength; difference comparing means for comparing the calculated difference with a predetermined acceptable range; and leak warning means for generating a leak warning for notification when the difference exceeds the acceptable range.

2. The leak detector according to claim 1, further comprising wavelength storing means for storing the measured wavelength at least until the next wavelength is measured, wherein said difference calculating means calculates the difference between the currently measured wavelength and the last measured wavelength, said last measured wavelength being used as the reference wavelength.

3. The leak detector according to claim 1, further comprising wavelength storing means for storing a first measured wavelength, wherein said difference calculating means calculates the difference between the first measured wavelength and the currently measured wavelength, said first measured wavelength being used as the reference wavelength; and said difference comparing means compares the difference with a predetermined acceptable range.

4. The leak detector according to claim 1, further comprising graph display means for displaying the wavelength measured for each of said pulse signals in a trend graph representation.

5. The leak detector according to claim 1, further comprising graph display means for displaying the difference calculated for each of said pulse signals in a trend graph representation.

6. The leak detector according to claim 1, wherein said pulse generating means emits said pulse signals comprised of ultrasonic waves, and said pulse detecting means detects said ultrasonic pulse signals.

7. The leak detector according to claim 1, further comprising a leak detection unit having at least said pulse generating means and said pulse detecting means; and a replaceable protection member for enclosing said leak detection unit, said protection member being transparent to the wave propagation.

8. The leak detector according to claim 1, wherein said leak detector comprises a plurality of said pulse generating means and/or a plurality of said pulse detecting means.

9. The leak detector according to claim 1, further comprising an extension tube for leading the liquid to said needle; and tube blocking means for blocking said extension tube when the difference exceeds the acceptable range.

10. The leak detector according to claim 1, further comprising imaging means for capturing an image of the human body at a position at which said needle is inserted; and image display means for displaying the captured image.

11. The leak detector according to claim 1, further comprising a leak detection unit including at least said pulse generating means and said pulse detecting means; a detector body formed separately from said leak detection unit and including at least said leak warning means, wherein said leak detection unit further includes radio transmitting means for transmitting a radio signal, and said detector body further includes radio receiving means for receiving the radio signal.

12. The leak detector according to claim 1, further comprising a leak detection unit having at least said pulse generating means and said pulse detecting means; and a transparent adhesive pad for removably adhering said leak detection unit on the surface of the human body, said adhesive pad being marked with a position of said needle.

13. The leak detector according to claim 12, wherein said adhesive pad is replaceably formed separately from said leak detection unit; and said adhesive pad is additionally marked with a position of said leak detection unit.

14. The leak detector according to claim 12, further comprising a replaceable protection member formed integrally with said adhesive pad for enclosing said leak detection unit, said protection member being transparent to the wave propagation.

15. The leak detector according to claim 11, wherein said leak detection unit further includes imaging means for capturing an image of the human body at a position at which said needle is inserted, and said detector body further includes image display means for displaying the captured image.

16. The leak detector according to claim 11, wherein said detector body further includes reception detecting means for detecting a receiving state of the radio signal; and state notifying means for notifying the detected receiving state.

17. The leak detector according to claim 16, wherein said detector body further includes reception warning means for generating a reception warning for notification when the detected receiving state falls below a predetermined state.

18. The leak detector according to claim 1, wherein said pulse generating means emits said pulse signals of infrared rays, and said pulse detecting means detects said infrared pulse signals.

19. The leak detector according to claim 18, further comprising an optical filter for passing the infrared rays exclusively at said wavelength therethrough to said pulse detecting means.

20. The leak detector according to claim 18, wherein said pulse generating means emits said pulse signals of infrared rays at a frequency which transmit through a particular organ of the human body and is reflected by a particular organ of the human body.

21. The leak detector according to claim 20, wherein said pulse detecting means detects only the infrared rays at said wavelength.

* * * * *